United States Patent
Abdou

(10) Patent No.: US 7,951,153 B2
(45) Date of Patent: May 31, 2011

(54) DEVICES AND METHODS FOR INTER-VERTEBRAL ORTHOPEDIC DEVICE PLACEMENT

(76) Inventor: Samy Abdou, San Diego, CA (US)

(*) Notice: Subject to any disclaimer, the term of this patent is extended or adjusted under 35 U.S.C. 154(b) by 876 days.

(21) Appl. No.: 11/245,466

(22) Filed: Oct. 5, 2005

(65) Prior Publication Data

US 2006/0111728 A1 May 25, 2006

Related U.S. Application Data

(60) Provisional application No. 60/616,100, filed on Oct. 5, 2004.

(51) Int. Cl.
*A61B 17/88* (2006.01)
(52) U.S. Cl. ........................................ 606/99; 606/86 A
(58) Field of Classification Search ................. 606/99, 606/86 A, 914, 104, 264, 279
See application file for complete search history.

(56) References Cited

U.S. PATENT DOCUMENTS

| | | | |
|---|---|---|---|
| 3,090,386 A * | 5/1963 | Babcock | 606/146 |
| 4,037,592 A * | 7/1977 | Kronner | 606/97 |
| 4,289,123 A | 9/1981 | Dunn | |
| 4,569,662 A * | 2/1986 | Dragan | 433/89 |
| 4,580,563 A * | 4/1986 | Gross | 606/79 |
| 4,722,331 A * | 2/1988 | Fox | 606/96 |
| 5,133,717 A | 7/1992 | Chopin | |
| 5,330,468 A * | 7/1994 | Burkhart | 606/96 |
| 5,334,205 A * | 8/1994 | Cain | 606/96 |
| 5,545,164 A | 8/1996 | Howland | |
| 5,609,634 A | 3/1997 | Voydeville | |
| 5,616,142 A | 4/1997 | Yuan et al. | |
| 5,645,599 A | 7/1997 | Samani | |
| 5,672,176 A | 9/1997 | Biedermann et al. | |
| 5,681,312 A | 10/1997 | Yuan et al. | |
| 5,928,233 A | 7/1999 | Apfelbaum et al. | |
| 5,993,449 A | 11/1999 | Schlapfer et al. | |
| 6,090,113 A * | 7/2000 | Le Couedic et al. | 606/914 |
| 6,123,707 A * | 9/2000 | Wagner | 606/86 A |
| 6,159,244 A | 12/2000 | Suddaby | |
| 6,306,136 B1 | 10/2001 | Beccelli | |
| 6,312,431 B1 | 11/2001 | Asfora | |
| 6,319,002 B1 * | 11/2001 | Pond | 433/89 |

(Continued)

FOREIGN PATENT DOCUMENTS

EP          77159  A1 *  4/1983

(Continued)

OTHER PUBLICATIONS

Denis, F. "The three column spine and its significance in the classification of acute thoracolumbar spinal injuries" Spine Nov.-Dec. 1983; 8(8):817-831.

*Primary Examiner* — Thomas C Barrett
*Assistant Examiner* — Christian Sevilla
(74) *Attorney, Agent, or Firm* — Fred C. Hernandez; Mintz Levin Cohn Ferris Glovsky and Popeo P.C.

(57) ABSTRACT

Disclosed are methods and devices for implanting an orthopedic device between skeletal segments, such as vertebrae, using limited surgical dissection. The implanted devices are used to adjust and maintain the spatial relationships of adjacent bones. The implanted device can be, for example, an artificial disc, a fusion cage or any other appropriate device for implantation between skeletal segments.

35 Claims, 14 Drawing Sheets

U.S. PATENT DOCUMENTS

| | | | |
|---|---|---|---|
| 6,319,257 B1 * | 11/2001 | Carignan et al. | 606/99 |
| 6,419,676 B1 | 7/2002 | Zucherman et al. | |
| 6,419,677 B2 | 7/2002 | Zucherman et al. | |
| 6,440,133 B1 * | 8/2002 | Beale et al. | 606/86 A |
| 6,451,019 B1 | 9/2002 | Zucherman et al. | |
| 6,451,020 B1 | 9/2002 | Zucherman et al. | |
| 6,524,315 B1 | 2/2003 | Selvitelli et al. | |
| 6,530,929 B1 | 3/2003 | Justis et al. | |
| 6,547,790 B2 | 4/2003 | Harckey, III et al. | |
| 6,599,294 B2 * | 7/2003 | Fuss et al. | 606/99 |
| 6,599,295 B1 | 7/2003 | Tornier et al. | |
| 0,229,347 A1 | 12/2003 | Sherman et al. | |
| 6,695,842 B2 | 2/2004 | Zucherman et al. | |
| 6,733,534 B2 | 5/2004 | Sherman | |
| 6,746,449 B2 * | 6/2004 | Jones et al. | 606/86 A |
| 6,755,841 B2 * | 6/2004 | Fraser et al. | 606/99 |
| 6,761,720 B1 | 7/2004 | Senegas | |
| 0,167,625 A1 | 8/2004 | Beyar et al. | |
| 6,821,277 B2 | 11/2004 | Teitelbaum | |
| 0,203,512 A1 | 9/2005 | Hawkins et al. | |
| 0,203,624 A1 | 9/2005 | Serhan | |
| 6,945,975 B2 | 9/2005 | Dalton | |
| 2002/0055741 A1 | 5/2002 | Schlapfer et al. | |
| 2002/0099386 A1 | 7/2002 | Beger et al. | |
| 2002/0161368 A1 * | 10/2002 | Foley et al. | 606/61 |
| 2002/0183755 A1 | 12/2002 | Michelson et al. | |
| 2003/0018389 A1 | 1/2003 | Castro et al. | |
| 2003/0074005 A1 | 4/2003 | Roth et al. | |
| 2003/0078583 A1 | 4/2003 | Biedermann et al. | |
| 2004/0044412 A1 * | 3/2004 | Lambrecht et al. | 623/17.16 |
| 2004/0133207 A1 | 7/2004 | Abdou | |
| 2004/0138671 A1 | 7/2004 | Zander et al. | |
| 2004/0204713 A1 | 10/2004 | Abdou | |
| 2005/0004573 A1 | 1/2005 | Abdou | |
| 2005/0021040 A1 | 1/2005 | Bertagnoli | |
| 2005/0119747 A1 | 6/2005 | Fabris Monterumici et al. | |
| 2005/0177163 A1 | 8/2005 | Abdou | |
| 2005/0192589 A1 * | 9/2005 | Raymond et al. | 606/99 |
| 2005/0245928 A1 * | 11/2005 | Colleran et al. | 606/61 |
| 2005/0273120 A1 | 12/2005 | Abdou | |
| 2005/0288669 A1 | 12/2005 | Abdou | |
| 2006/0036240 A1 | 2/2006 | Colleran et al. | |
| 2006/0074488 A1 | 4/2006 | Abdou | |
| 2006/0084988 A1 | 4/2006 | Kim | |
| 2006/0149278 A1 | 7/2006 | Abdou | |
| 2006/0217710 A1 | 9/2006 | Abdou | |
| 2006/0229615 A1 | 10/2006 | Abdou | |
| 2007/0093828 A1 | 4/2007 | Abdou | |
| 2007/0106383 A1 | 5/2007 | Abdou | |
| 2007/0123884 A1 | 5/2007 | Abdou | |

FOREIGN PATENT DOCUMENTS

| | | |
|---|---|---|
| WO | 2004/032726 | 4/2004 |
| WO | 2004/062482 | 7/2004 |
| WO | 2004/093702 | 11/2004 |
| WO | 2005/077288 | 8/2005 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

* cited by examiner

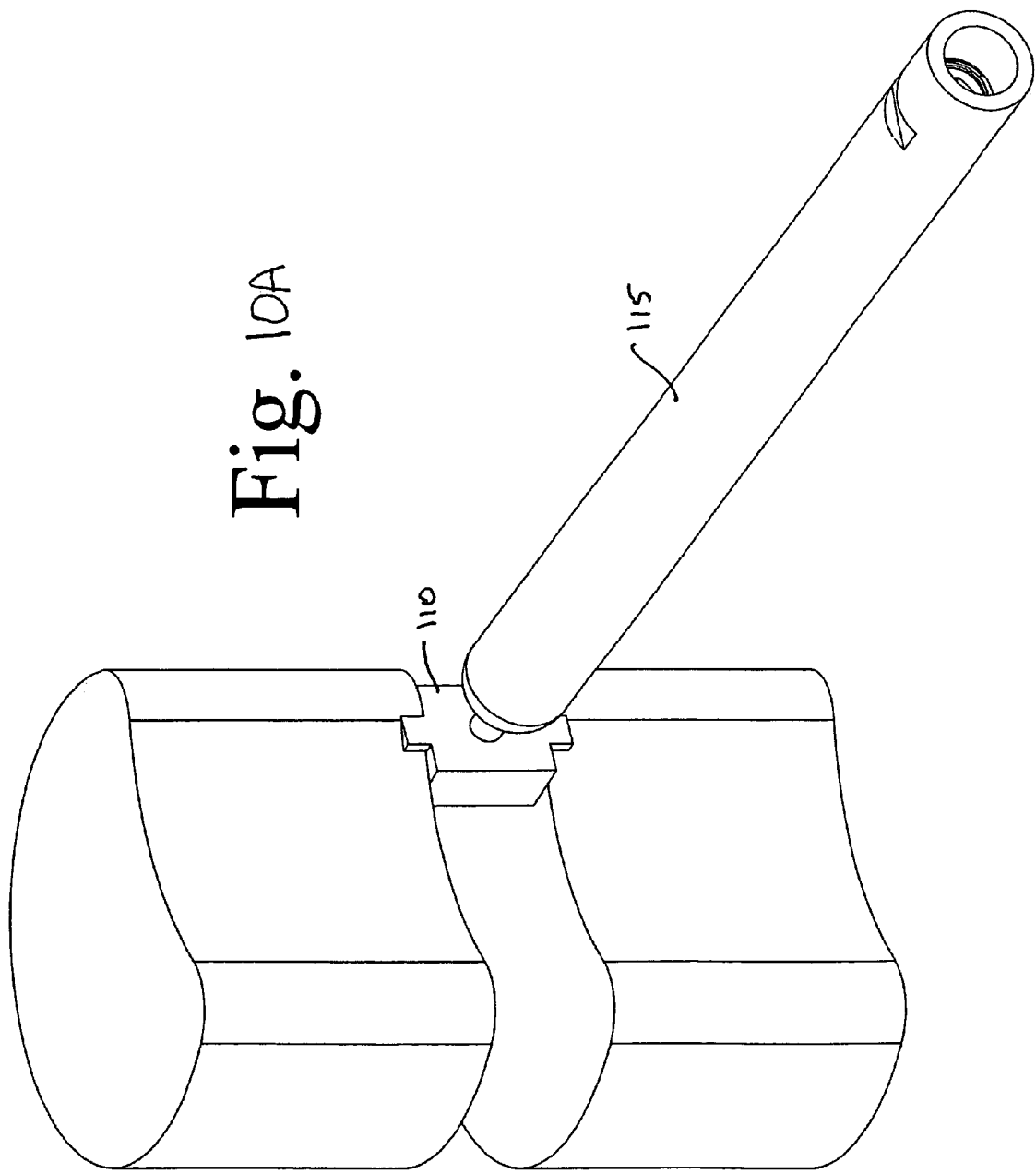

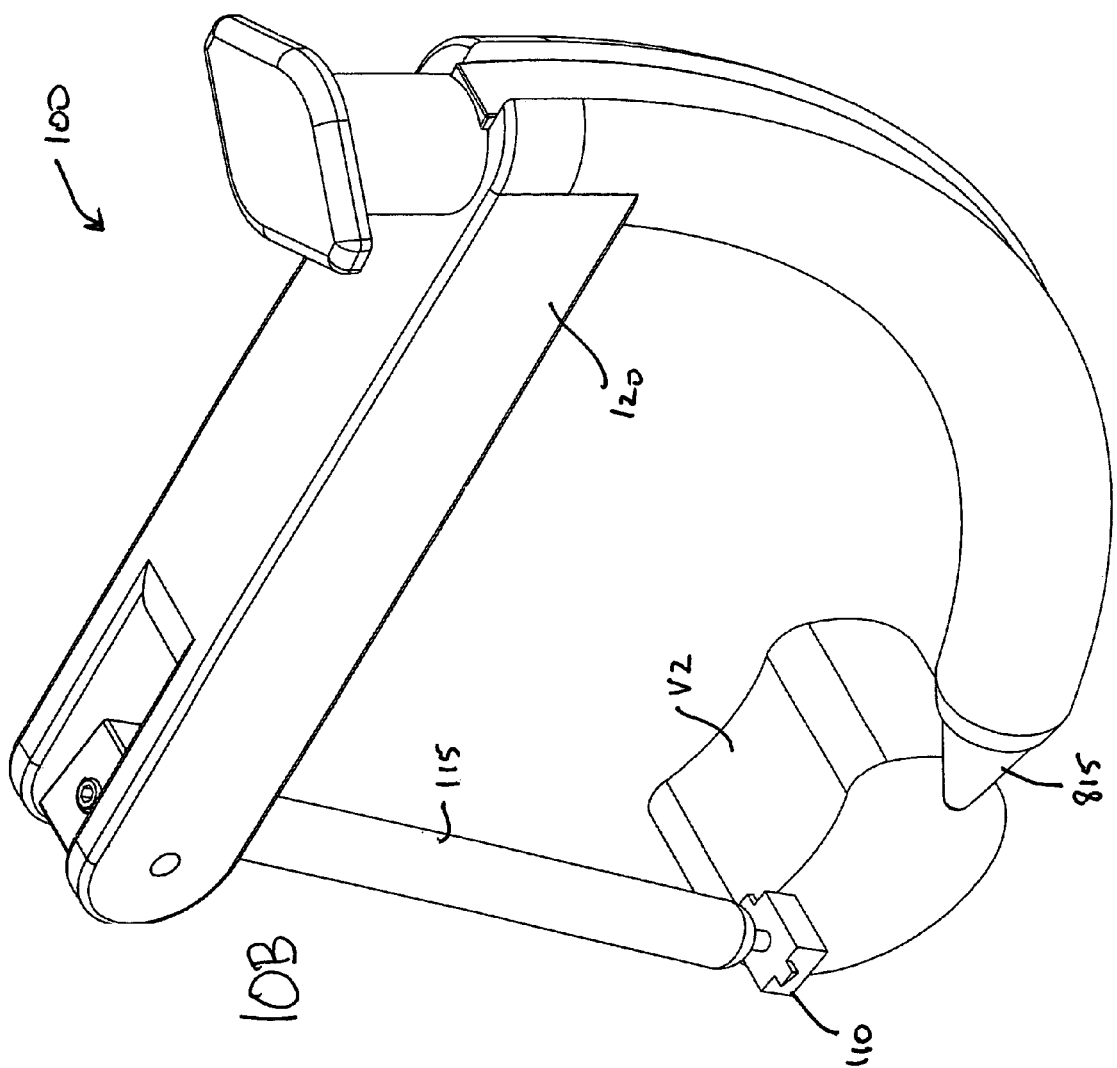

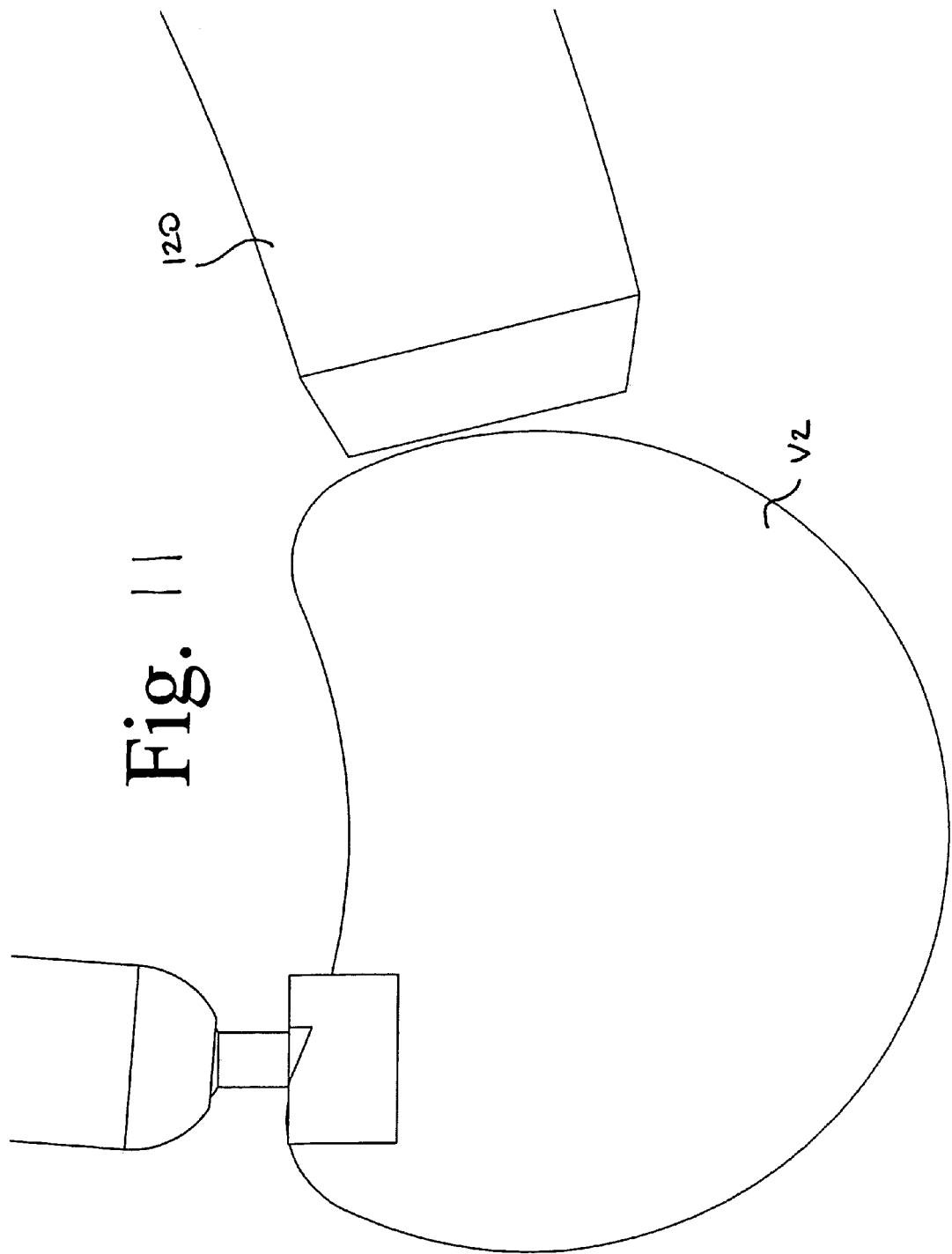

DEVICES AND METHODS FOR INTER-VERTEBRAL ORTHOPEDIC DEVICE PLACEMENT

PREFERENCE TO PRIORITY DOCUMENT

This application claims priority of U.S. Provisional Patent Application Ser. No. 60/616,100, filed Oct. 5, 2004. Priority of the aforementioned filing date is hereby claimed, and the disclosure of the Provisional Patent Application is hereby incorporated by reference in its entirety.

BACKGROUND

The disclosure relates to devices and methods for implantation of an orthopedic device between skeletal segments using limited surgical dissection. The implanted devices are used to adjust and maintain the spatial relationship(s) of adjacent bones. Depending on the design of the implant, the skeletal segments may be immobilized or motion between them may be preserved.

Surgical reconstructions of the bony skeleton are common procedures in current medical practice. Regardless of the anatomical region or the specifics of the reconstructive procedure, many surgeons employ an implantable device between bony segments in order to adjust, align and maintain the spatial relationship(s) between them.

Placement of an inter-vertebral device within the spine may be performed through various approaches. Access to the anterior aspect of the spine provides a direct route for device placement. However, since the spine is situated posteriorly within the body cavity, an anterior approach requires dissection through the many vital tissues that lie anterior to the spine. Likewise, a lateral approach also requires extensive dissection of the body cavity. Both approaches are more difficult in the thoracic and lumbar spine, since these body cavities contain far more tissue anterior and lateral to the spine.

A posterior approach provides ready access to the posterior aspect of the spine through an operative corridor that is familiar to all spine surgeons. Unfortunately, the nerve elements are situated posterior to the inter-vertebral space and will limit access to that space. Hence, use of the posterior approach for the placement of any sizable device within the inter-vertebral space risks permanent neurologic injury.

SUMMARY

In view of the proceeding, there is a need for devices and methods for delivery of inter-vertebral implants that do not require extensive dissection of normal tissues or significant retraction of the nerve elements. Such devices and methods provide ease of use as well as a safe and familiar surgical approach that maximizes the likelihood of optimal device placement within the inter-vertebral space.

The spine is posteriorly situated within the body cavity and can be readily reached with minimal tissue dissection using a posterior skin incision. This approach is direct, safe, simple and familiar to all spine surgeons. Unfortunately, the neural elements that reside within the spinal canal will permit only limited access to the anteriorly-placed inter-vertebral disc space. Access is gained through a small window lateral to the nerves. While this window can be used to safely remove disc material and place small inter-vertebral devices, attempts at placement of any sizable device risks permanent nerve injury.

Disclosed is a device that can accurately place a sizable implant within the inter-vertebral space without the extensive tissue dissection currently required to access this region.

The spine is approached through a posterior incision permitting access to the inter-vertebral disc space through the window lateral to the nerves. A discectomy is performed and the disc material is removed piecemeal. An instrument is placed into the disc space through the lateral window. The distal end of the instrument is attached to a curvilinear guide. The guide arm is then rotated about the distal end of the instrument until the tip of the guide arm abuts the side of the disc space. In this way, the guide arm can be used to guide an orthopedic device into the disc space with minimal tissue dissection. In other embodiments, instruments are attached to the spinous processes, pedicles or other bony landmarks. The guide arm is connected to the distal end of the instrument(s) and the guide arm is rotated into position.

In one aspect, there is disclosed an instrument for implanting an implant device in a space between a pair of skeletal segments. The instrument can comprise a mount having a distal end mountable between the pair of skeletal segments, and an insertion device pivotably attached to a proximal end of the mount. The insertion device is pivotable to an orientation so as to deliver an implant into the space between the pair of skeletal segments.

In another aspect, there is disclosed an instrument for implanting an implant device into a space between skeletal segments. The instrument can comprise an insertion device having a delivery shaft, wherein the insertion device can be pivotably mounted in a predetermined spatial relationship relative to the space between the skeletal segments. The insertion device pivots to a delivery orientation such that the delivery shaft provides a pathway for the delivery of an orthopedic device into the space between the skeletal segments.

In another aspect, there is disclosed a device for use in a surgical procedure, comprising at least one anchor that anchor relative to a target location; and an insertion device connected to the at least one anchor, the insertion device movable in a fixed geometric relation to the at least one anchor so as to place an implant at the target location.

In another aspect, there is disclosed a device for use in a surgical procedure, comprising at least one anchor that anchor relative to a target location and an insertion device movably attached to the anchor. The insertion device is movable in a fixed geometric relationship relative to the at least one anchor so as to place the implant in the target location. The position of target location is defined using x-ray guidance.

The placement system described herein provides an easy and reliable way of placing sizable orthopedic device(s) within the inter-vertebral with minimal tissue dissection. The implanted devices may include, for example, artificial discs, fusion cages or any other appropriate device.

These and other features will become more apparent from the following description and certain modifications thereof when taken with the accompanying drawings.

BRIEF DESCRIPTION OF THE DRAWINGS

FIG. 10A shows a perspective view of the mount attached to a disc space.

FIG. 10B shows a perspective view of the device with the insertion device fully rotated toward the disc space such that a tapered tip is positioned adjacent the lateral side of the disc space between the vertebrae.

FIG. 11 shows an enlarged, close-up view with a distal tip of the insertion device positioned adjacent the lateral side of the disc space between the vertebrae

DETAILED DESCRIPTION

Disclosed are methods and devices for implanting an implant device (such as an orthopedic device) between skeletal segments (such as vertebrae), using limited surgical dissection. The implanted devices are used to adjust and maintain the spatial relationship(s) of adjacent bones. The implanted device can be, for example, an artificial disc, a fusion cage or any other appropriate device for implantation between skeletal segments.

Figure 1:
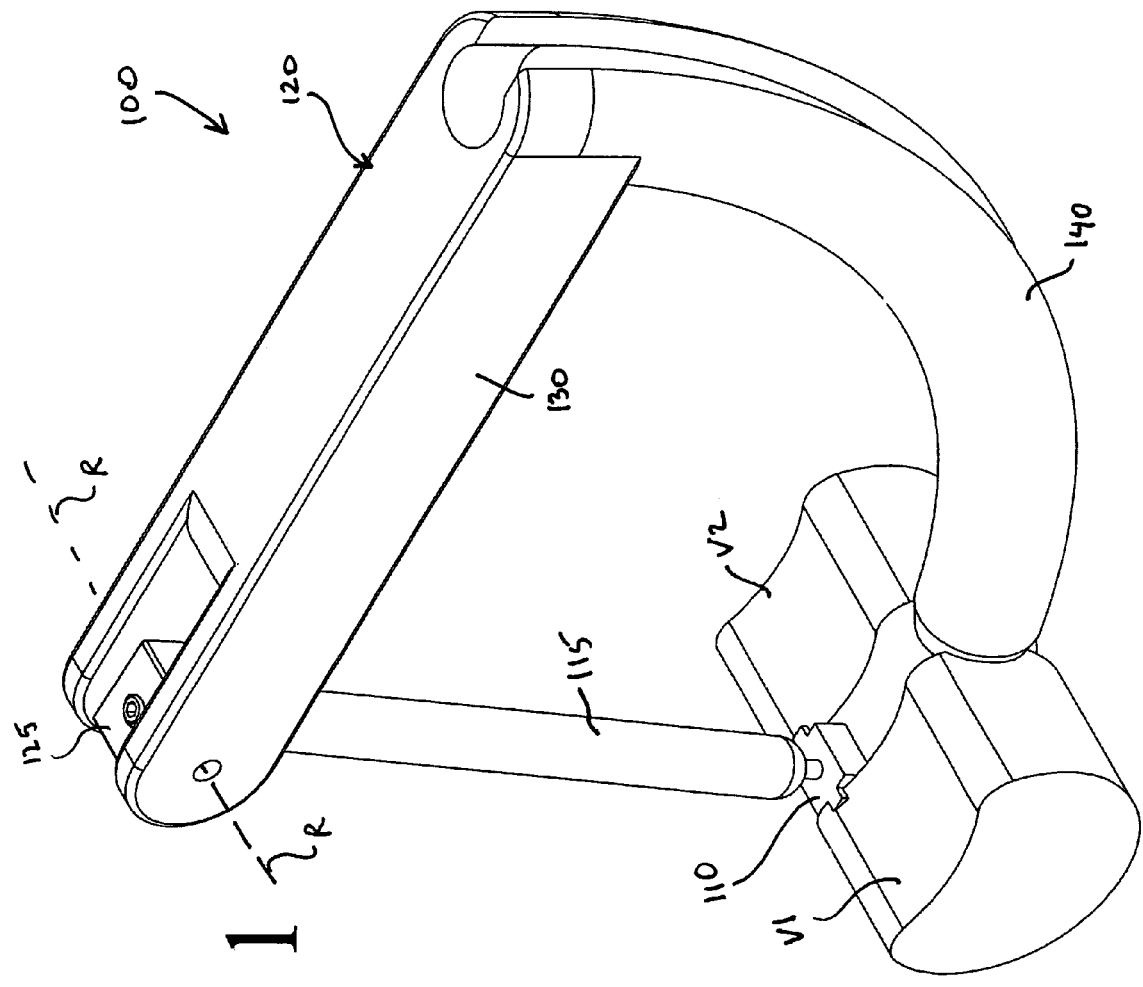
FIG. 1 shows a perspective, assembled view of a device for implanting an orthopedic device between skeletal segments, such as between a first vertebra V1 and a second vertebra V2.
Figure 2:
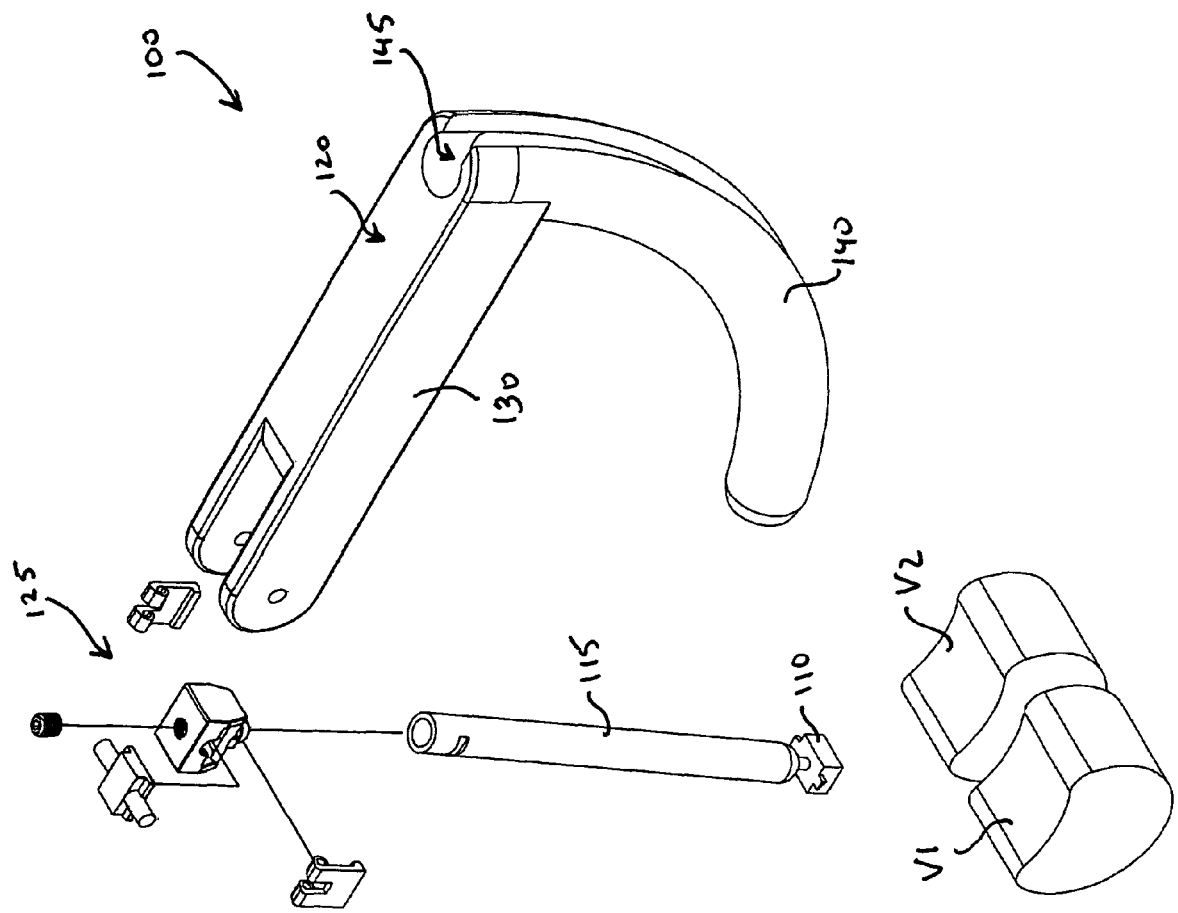
FIG. 2 shows the device 100 in an exploded state and uncoupled from the first vertebra V1 and second vertebra V2.

FIG. 1 shows a perspective, assembled view of a device 100 for implanting an orthopedic device between skeletal segments, such as between a first vertebra V1 and a second vertebra V2. In FIG. 1, a coupler of the device 100 is positioned in a disc space between the first vertebra V1 and second vertebra V2. FIG. 2 shows the device 100 in an exploded state and uncoupled from the first vertebra V1 and second vertebra V2. For clarity of illustration, the vertebrae are represented schematically and those skilled in the art will appreciate that actual vertebrae include anatomical details not shown in FIG. 1. Moreover, although described in the context of being used with vertebrae, it should be appreciated the device 100 and associated methods can also be used with other skeletal segments.

The device 100 includes a coupler 110, a elongate mount 115, and an insertion device 120 that is pivotably attached to a proximal end of the mount 115 via an attachment member 125. The mount 115 is used to attach the insertion device 120 to the coupler 110.

The coupler 110 is a device that anchors to a predetermined location relative to a skeletal segment. For example, the coupler 110 can anchor to the one or more of the vertebrae or to the disc space between a pair of vertebrae. In one embodiment, the coupler 110 is sized and shaped to be positioned within and removably secured within the disc space between the two vertebrae. The coupler 110 can have any shape that is configured to be attached between two vertebrae. In the illustrated embodiment, the coupler 110 is rectangular shaped with a pair of outwardly-extending posts that abut at least a portion of the vertebrae.

With reference still to FIGS. 1 and 2, a mount 115 extends outwardly from the coupler 110. The mount 115 is an elongate member, such as a post, having a distal end attached to the coupler 110 and a proximal end pivotably attached to the insertion device 120. The mount 115 includes an inner member and an outer member, as described in detail below with reference to FIGS. 3 and 4.

The insertion member 120 is pivotably attached to the proximal end of the mount 115. The insertion member 120 includes a straight or substantially straight portion 130 that extends outwardly from the proximal end of the mount, and a curved portion 140 that curves toward the coupler 110 from an outward tip of the straight portion 130. The curved portion 140 includes a guide shaft 145 that extends through the curved portion 140 along the entire length of the curved portion 140. The radius of curvature of the curved portion 140 can vary. In one embodiment, the radius of curvature is approximately equal to the length of the straight portion 130. As described in detail below, the curved portion 140 acts as a guide for guiding an orthopedic device to a position between the skeletal segments.

As mentioned, an attachment member 125 pivotably attaches the insertion member 120 to the proximal end of the mount 115. The attachment member 125 is configured to permit the insertion member 120 to pivot about a pivot axis R (shown in FIG. 1). An exemplary embodiment of the attachment member 125 is described in detail below, although it should be appreciated that the structural configuration of the attachment member 125 can vary.

Figure 3:
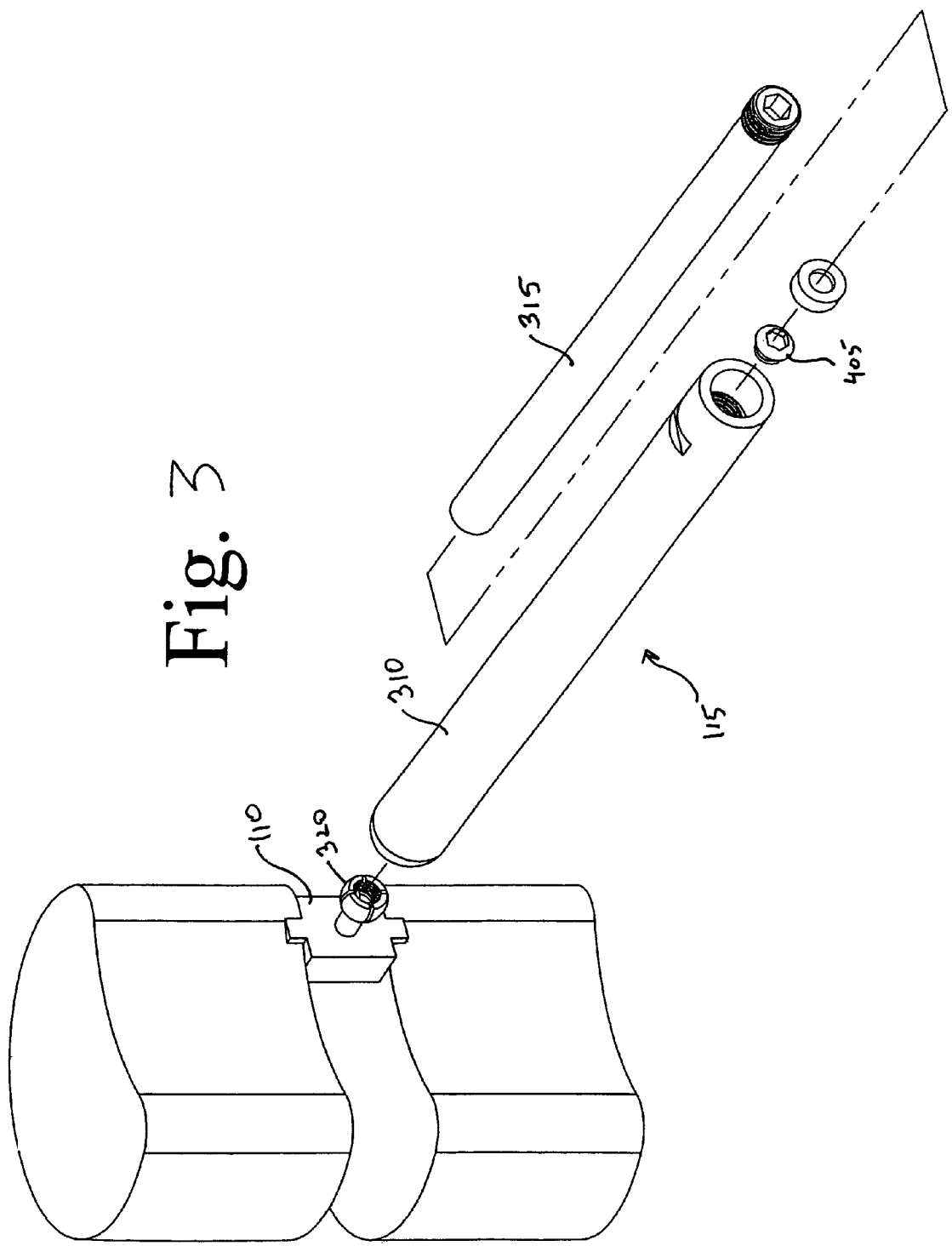
FIG. 3 shows an exploded view of a mount that attaches the insertion member of the device to a coupler of the device.

FIG. 3 shows an exploded view of the mount 115 that attaches the insertion member 120 to the coupler 110. For clarity of illustration, the insertion member 120 is not shown in FIG. 3. As mentioned, the mount 115 includes an outer member 310 and an inner member 315 that can be slidably and axially positioned inside the outer member 310. The outer member 310 is sized to fit over a head 320 of the coupler 110 in a press fit fashion to thereby permit the mount 115 to be removably coupled to the coupler 110.

Figure 4:
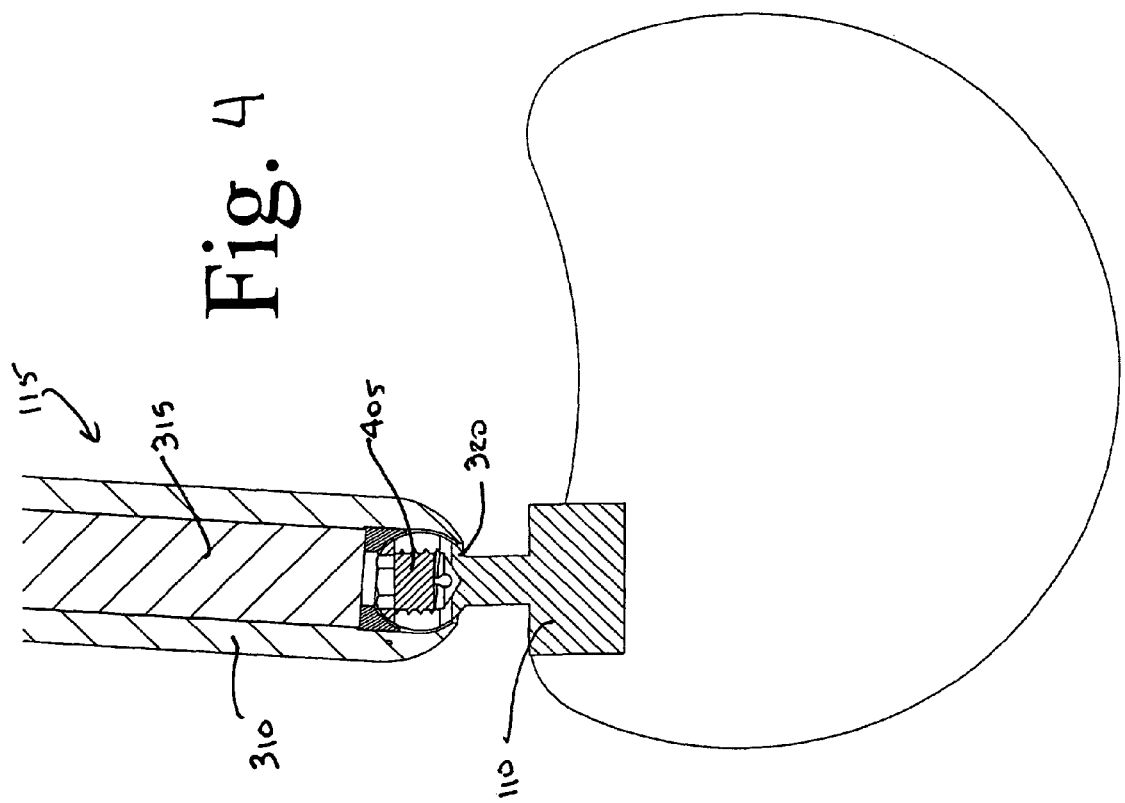
FIG. 4 shows a cross-sectional view of the mount coupled to the coupler.

FIG. 4 shows a cross-sectional view of the mount 115 coupled to the coupler 110. The outer member 310 is positioned over the head 320 such that the mount 115 extends outwardly from the coupler 110. Moreover, the outer member 310 is positioned over the head 320 such that the mount 115 can be pivoted relative to the coupler 110. A set screw 405 can be set into the head 320 of the coupler 110 to secure the mount 115 to the coupler 110. The inner member 315 is then inserted into the outer member 315 over the set screw 405. In this manner, the mount 115 is pivotably attached to the coupler 110.

Figure 5:
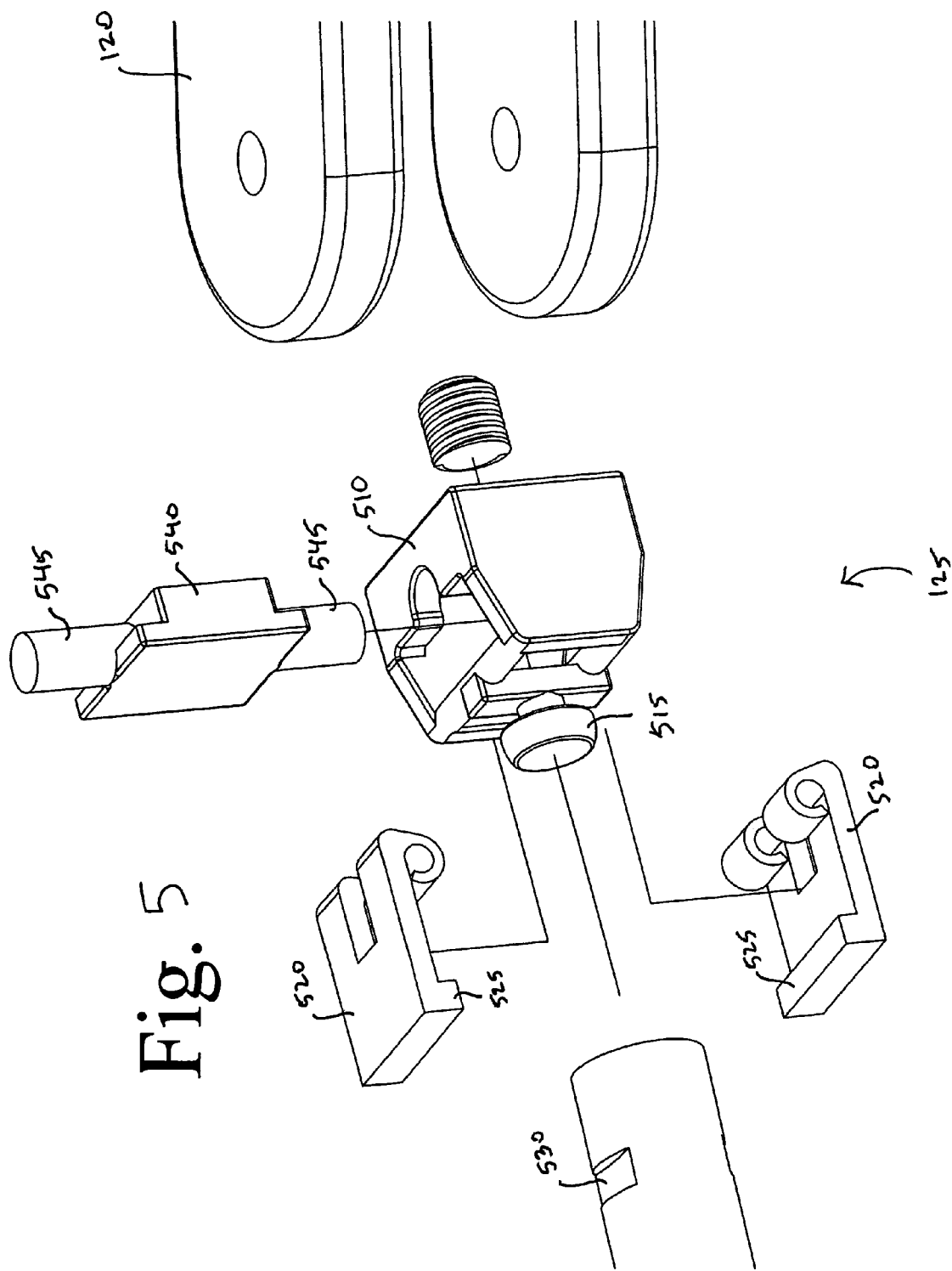
FIG. 5 shows an enlarged, exploded view of an attachment member positioned adjacent an attachment region of the insertion device.
Figure 6:
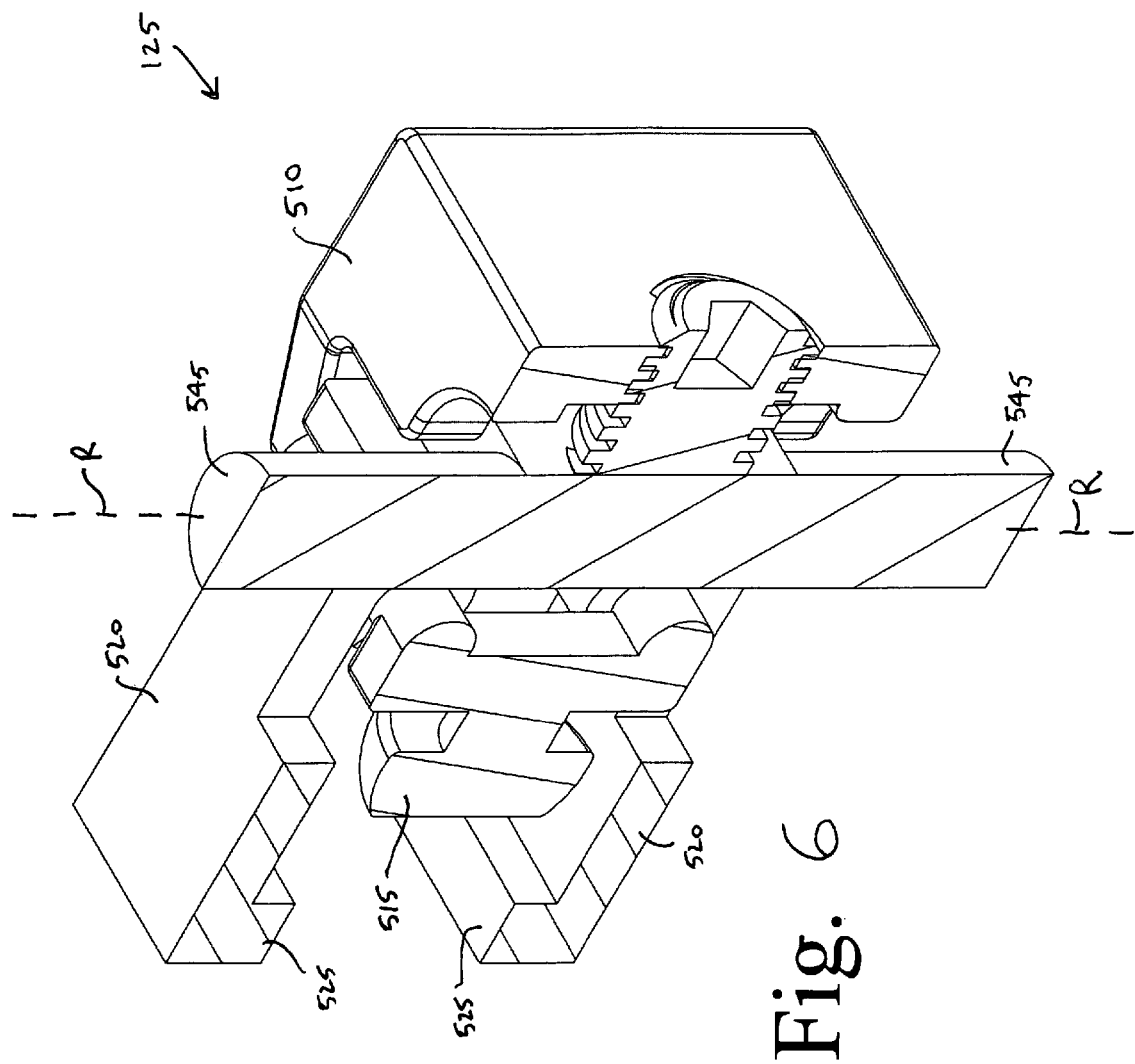
FIG. 6 shows a perspective, cross-sectional, assembled view of the attachment member.

As mentioned, the attachment member 125 is used to pivotably attach the insertion device 120 to the proximal end of the mount 115. FIG. 5 shows an enlarged, exploded view of the attachment member 125 positioned adjacent an attachment region of the insertion device 120. FIG. 6 shows a perspective, cross-sectional, assembled view of the attachment member 125. The attachment member 125 includes a main body 510 having a rounded protrusion 515 that can be positioned inside the proximal end of the mount 115. A pair of side walls 520 having inwardly extending teeth 525 are positioned on opposite sides of the main body 510. As mentioned, the structural configuration of the attachment member 125 can vary and is not limited to the embodiment described herein.

With reference to FIG. 5, the attachment member 125 is attached to the mount 115 by inserting the rounded protrusion 515 into the proximal end of the mount 115. The two side walls 520 are positioned on either side of the mount 115 such that each tooth 525 engages a corresponding slot 530 on the mount 515. In this manner, the attachment member 125 is attached to the mount 115.

With reference to FIGS. 5 and 6, a pivot rod member 540 is positionable inside the main body 510. The pivot rod member 540 includes a pivot rod 545 that protrude outwardly from opposed sides of the main body 510 when the pivot rod member 540 is positioned inside the main body 510. The pivot rod 545 can be inserted into a pair of apertures 555 on the insertion device 120 to pivotably couple the insertion device 120 to mount 115 via the attachment member 125. The pivot rod 545 defines the pivot axis R (FIGS. 1 and 6) for pivoting of the insertion device 120.

Figure 7:
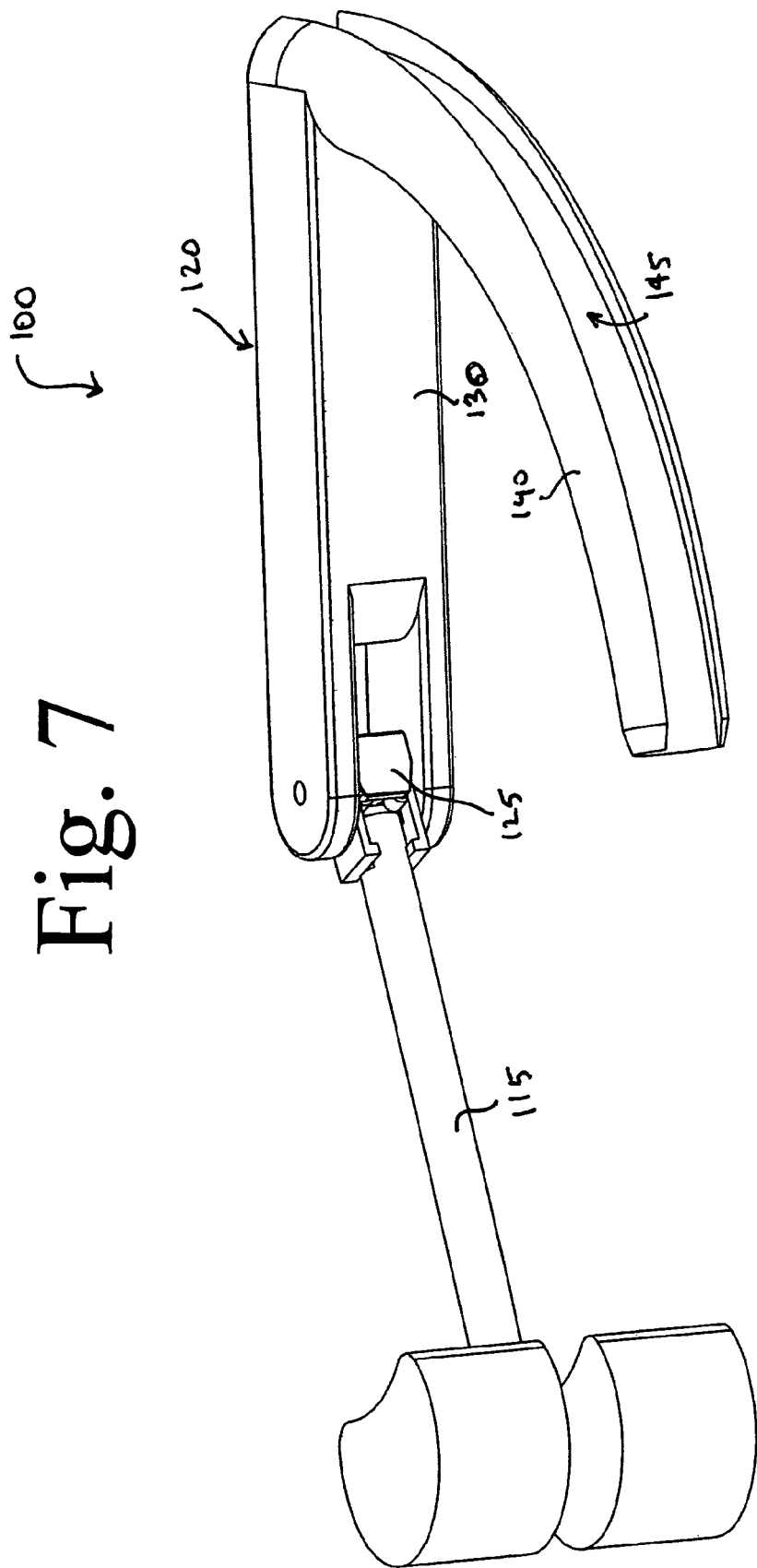
FIG. 7 shows a perspective view of the device with the insertion device pivotably attached to the mount via the attachment member.

FIG. 7 shows a perspective view of the device 100 with the insertion device 120 pivotably attached to the mount 115 via the attachment member 125. As mentioned, the insertion device 120 includes a curved portion 140 having a guide shaft 145 that extends through the length of the curved portion 140. The guide shaft 145 has an open end such that the guide shaft 145 is visible from the side of the curved portion 140.

Figure 8:
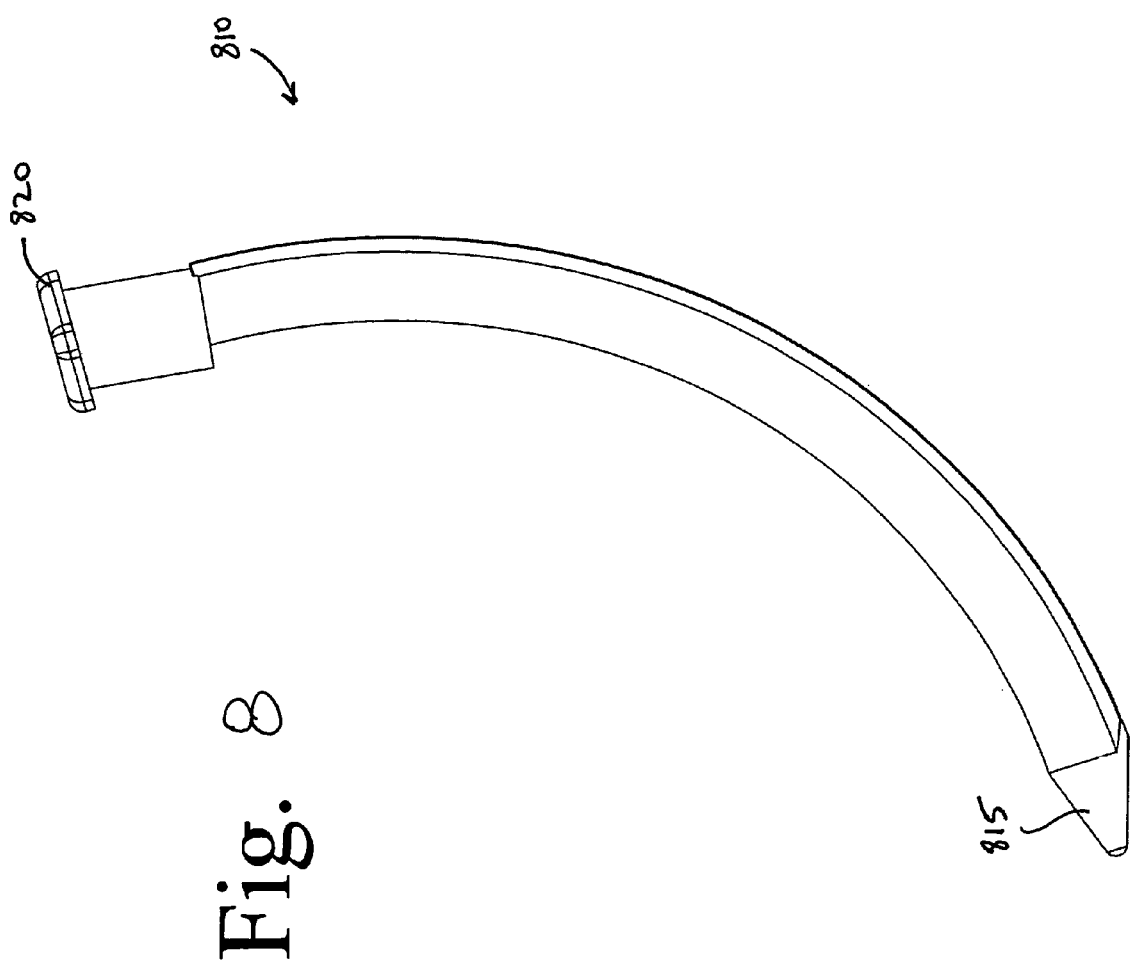
FIG. 8 shows a side view of an elongate plunger of the device.
Figure 9:
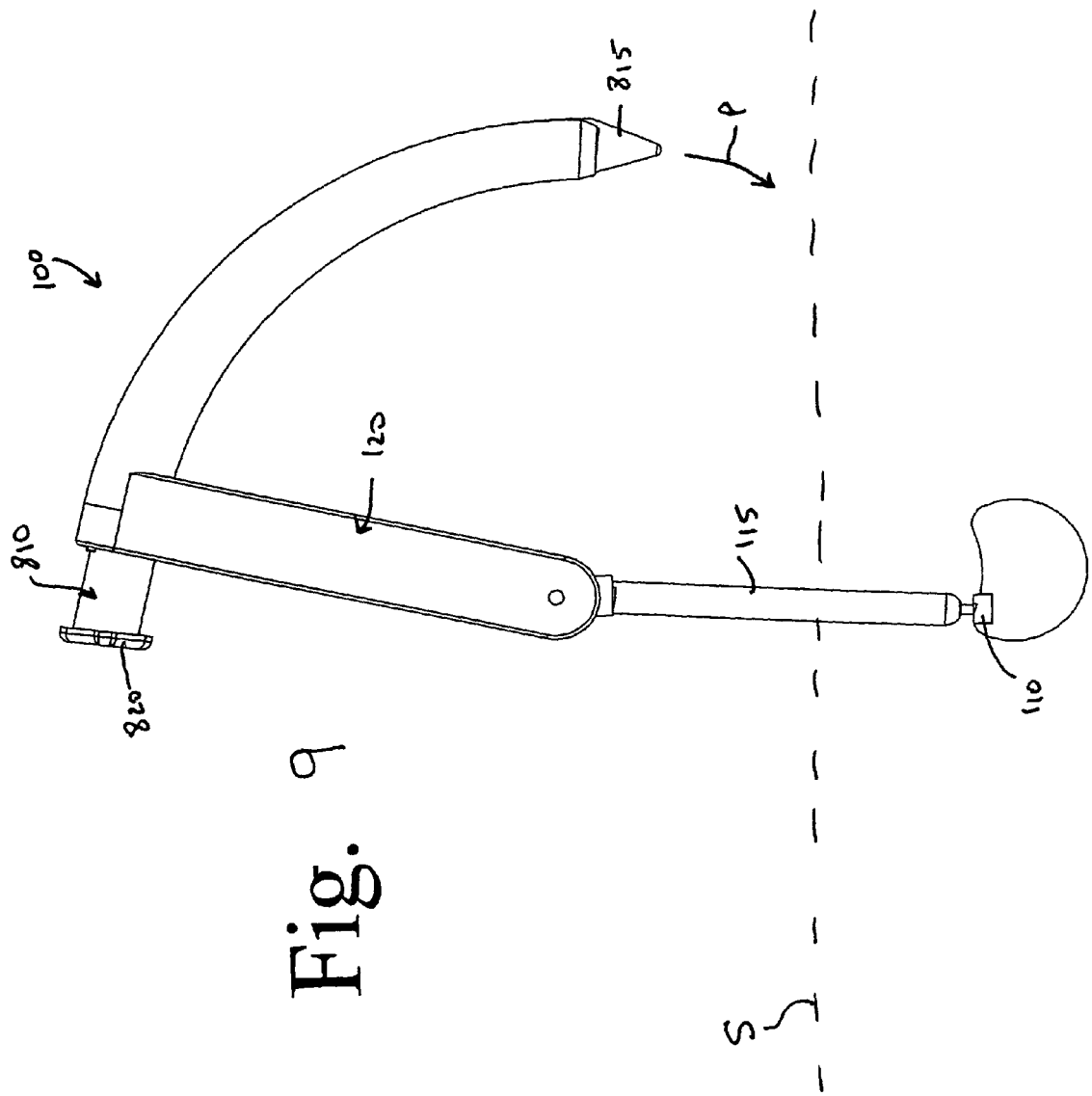
FIG. 9 shows a side view of the device with the plunger positioned inside a slot of the insertion device.

FIG. 8 shows a side view of an elongate plunger 810 that slidably fits within the guide shaft 145 of the curved portion 140 of the insertion device 120. The plunger 810 has a tapered tip 815 on a distal end and a handle 820 on a proximal end. The plunger 810 is inserted into the guide shaft 145 by inserting the tapered tip 815 into an entryway (shown in FIG. 1) of the guide shaft 145 and sliding the plunger 810 into the guide shaft 145. When the plunger 810 is fully positioned in the guide shaft 145, the handle 820 protrudes out of one end of the guide shaft 145 and the tapered tip 815 protrudes out of the opposite end of the guide shaft 145. FIG. 9 shows a side view of the device 100 with the plunger 810 positioned inside the slot 140 of the insertion device 120.

An exemplary method of using the device 100 is now described in the context of using the device 100 to implant of an implant device between a pair of vertebrae. First, the spine is approached through a posterior incision permitting access to the inter-vertebral disc space through a window lateral to the nerves. A discectomy is performed and the disc material is removed piecemeal.

The coupler 110 of the device 100 is then attached to an attachment point. It should be appreciated that the attachment point need not be the disc space itself. The coupler 110 can be attached directly to one of the vertebrae or to some other reference location. In an exemplary embodiment, the coupler 110 is tightly fitted into the disc space between the vertebrae such that the coupler is anchored in the disc space. During this step, the insertion device 120 can be disattached from the mount 115 such that the proximal end of the mount 115 is free and the distal end of the mount 115 is attached to the coupler 110. At this stage, the mount 115 extends outwardly from the coupler 110, as shown in FIG. 10A.

After the distal end of the mount 115 is tightly fitted into the disc space, a target location is identified and localized, wherein the target location is the location where the implant device is to be implanted. The mount 115 is positioned such that the insertion device 120, when attached to the mount 115, can be pivoted to an orientation that provides a guide toward the target location for delivery of the implant device. In this regard, the mount 115 can be aimed toward the target location in a variety of manners. For example, one or more x-ray image can be taken of the target location and the target location localized using the x-ray images by iteratively moving the mount so that the insertion device provides a guide toward the target location. A pointer, such as an elongate needle, can be used in combination with the one or more x-ray images to aid in pointing the mount and insertion device toward the target location. The mount can also be attached directly at the target location (such as in the disc space) to facilitate localization of the target location. The insertion device 120, when connected to the mount 115 and coupler 110, is movable in a fixed geometric relationship to the mount and coupler 110 so as to place the implant at the target location.

In one embodiment, the free, proximal end of the mount 115 is moved into the spinal midline by pivoting the mount about its attachment location with the coupler 110. The spinous process is easily located on the posterior aspect of the spine and it marks the midline. In another embodiment, another portion of the device clamps onto the spinous processes and act as a marker of midline the attachment point for the swing arm.

Once the mount 115 is positioned in the desired orientation (such as with the free end of the mount along the spinal midline), the inner member 315 (FIG. 3) of the mount 115 is rotated relative to the outer member 310. This locks the position and orientation of the mount. At this stage, the mount is positioned along the spinal midline.

In addition, the mount 115 is now appropriately positioned and locked in this position. The insertion device 120 can now be attached to the free, proximal end of the mount 115. At this stage, the assembled device 100 is coupled to the disc space such that the mount 115 extends outwardly from the disc space and the insertion device 120 is pivotably mounted to the proximal end of the mount 115

The plunger 810 is then slid into the curved guide shaft 145 of the insertion device 120, as shown in FIG. 9. The handle 820 of the plunger 810 is then used to push the insertion device 120 such that the insertion device 120 rotates toward the skin S about the pivot axis R, as represented by the arrow P in FIG. 9. As the rotational movement occurs, the tapered tip 815 of the plunger 810 moves toward the skin S and eventually abuts the skin S. A small skin incision is made and the insertion device 120 is then rotated further until the tapered tip 815 contacts the lateral side of the disc space.

FIG. 10B shows a perspective view of the device 100 with the insertion device 120 fully rotated toward the disc space such that the tapered tip 815 is positioned adjacent the lateral side of the disc space between the vertebrae. For clarity of illustration, the skin S is not shown in FIG. 10 and the first vertebra V1 is also not shown.

The plunger 810 is now removed from the guide shaft 145 such that the slot is empty. FIG. 11 shows an enlarged, close-up view with the distal tip of the insertion device 120 positioned adjacent the lateral side of the disc space between the vertebrae. Although shown adjacent to the posterior end of the disc space, it should be appreciated that the insertion device 120 can be positioned adjacent to any part of the disc space.

At this stage, the guide shaft 145 provides a pathway to the target location (e.g., the disc space). An implant device can now be delivered into the disc space by sliding the implant device through the guide shaft 145 in the curved portion 140 of the insertion device 120. In this way, an orthopedic device can be precisely delivered into the inter-vertebral disc space using the posterior surgical approach with minimal tissue dissection or nerve retraction. This method provides a minimally invasive way of implanting orthopedic devices into the disc space.

Figure 12:
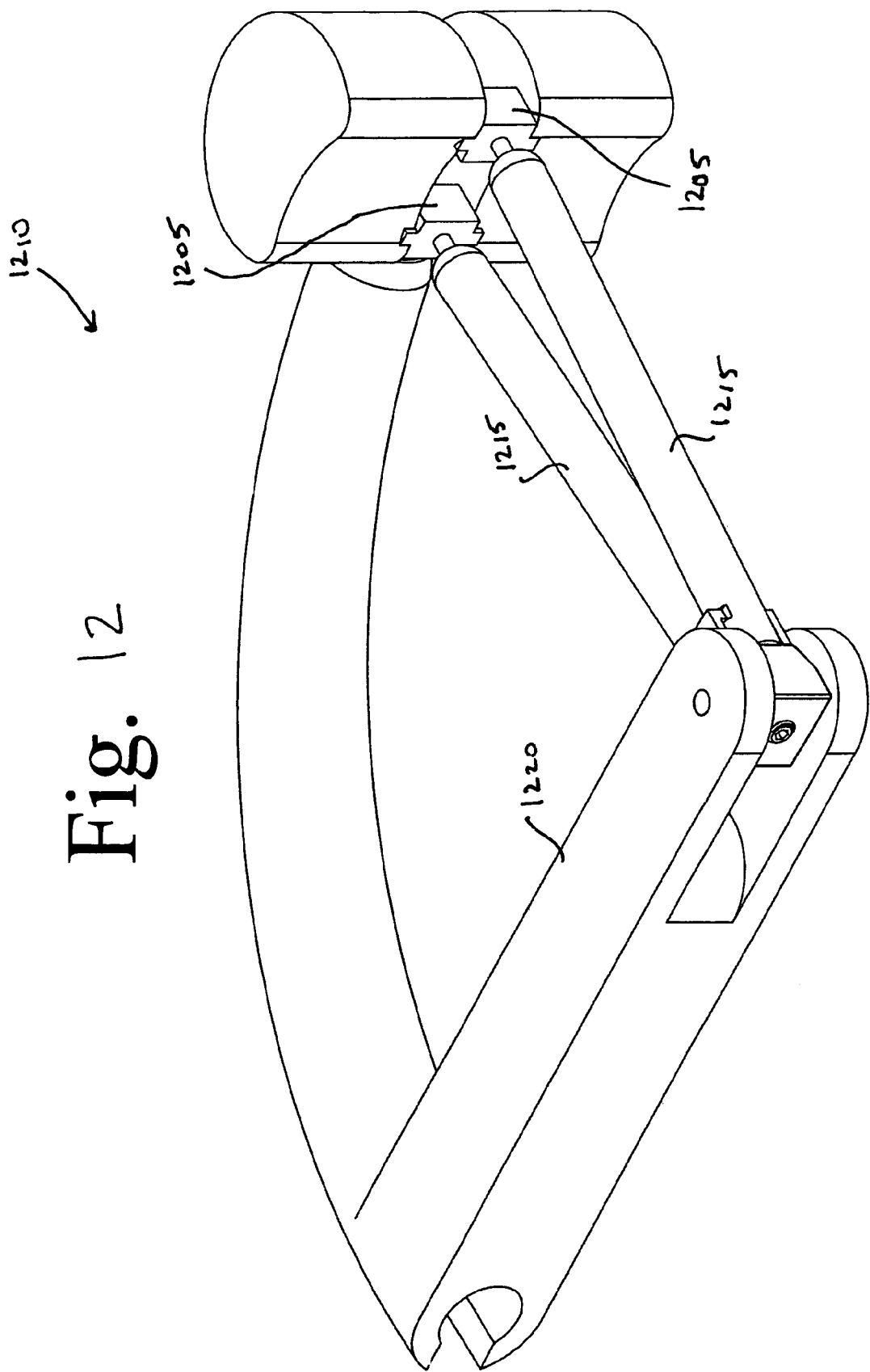
FIG. 12 shows a perspective, assembled view of a second embodiment of the device.
Figure 13:
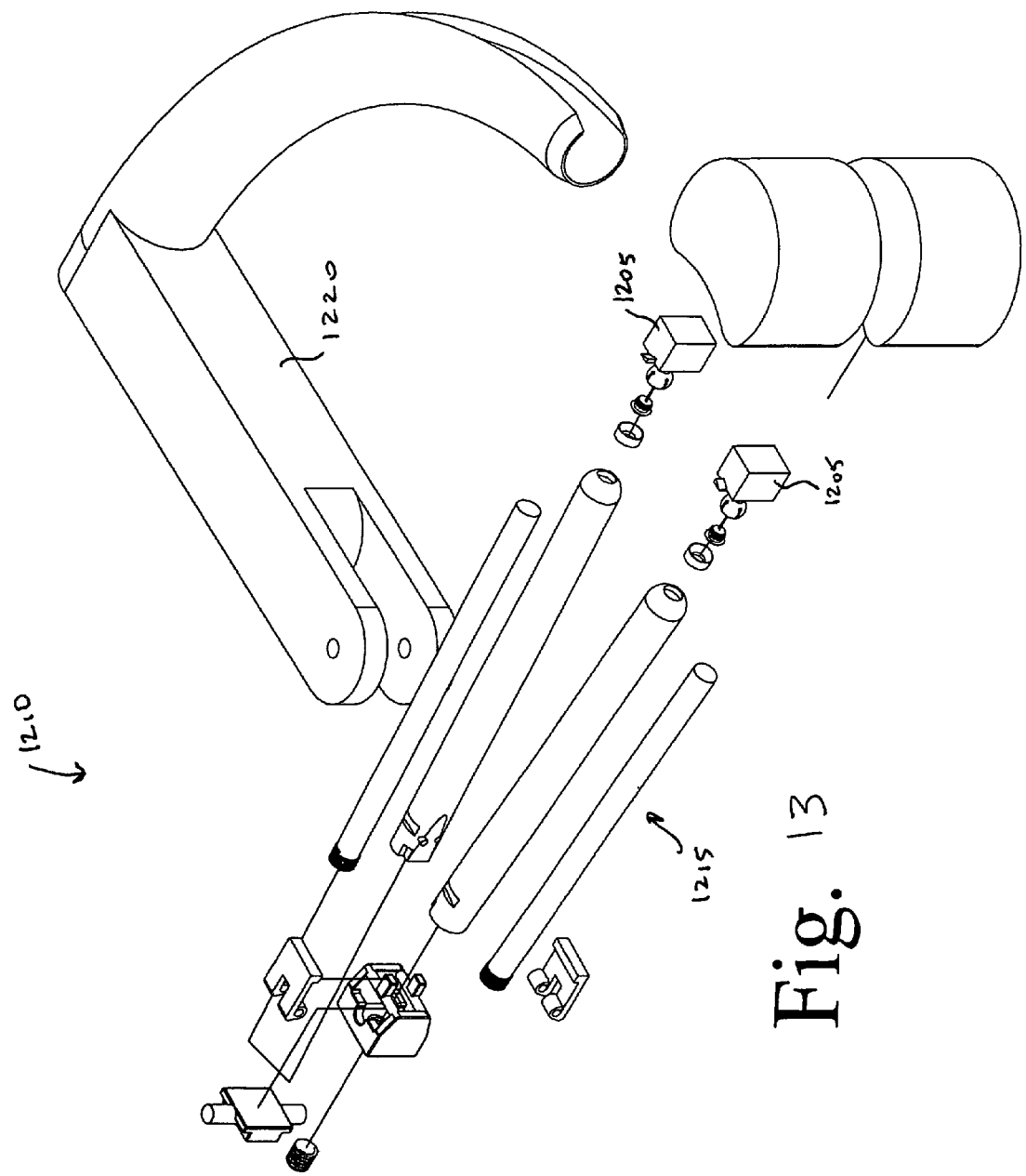
FIG. 13 shows an exploded view of the second embodiment of the device.

FIG. 12 shows a perspective, assembled view of a second embodiment of the device, referred to as device 1210. FIG. 13 shows an exploded view of the second embodiment of the device 1210. In this embodiment, the device 1210 includes a pair of mounts 1215 that anchor the device 1210 within the disc space between two vertebrae. As in the previous embodiment, the mounts 1215 are elongate rods that are each attached at one end to a coupler 1205. The proximal ends of the mounts 1215 are joined to an insertion device 1220 in a pivoting manner using an attachment member 1225. Since both mounts 1215 are of equal length, the distal ends are in the spinal midline.

It should be appreciated that the configuration of the devices and the methods described herein can vary. For example, in another embodiment, a member is attached onto the spinous processes and define the midline. An instrument is placed into the disc space, coupled to the spinous process member and used to determine the plane of the disc space. The insertion device is then attached onto one or both of these segments and rotated onto the lateral aspect of the disc space as illustrated above. In other embodiments, the pedicles or other bony landmarks are used as attachment points. The insertion device is then fixed to the attached member and rotated onto the lateral aspect of the disc space as previously described.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An instrument for implanting an orthopedic implant in a target space between a pair of skeletal segments, comprising:
   a first mount comprising an elongate body having a distal end mountable at a defined anatomical position relative to the target space;
   an implant insertion device pivotably attached to a first end of the mount, wherein the insertion device is pivotable to an orientation so as to deliver the implant into the space between the pair of skeletal segments, and wherein the insertion device comprises a straight member rotatably attached to the first end of the mount, and a curved elongate body extending from the straight member, wherein the curved elongate body has a proximal end attached to the straight member and wherein the curved elongate body contains an arcuate internal bore extending from a proximal opening at a proximal region of the curved elongated body to a distal opening at a distal region of the curved elongated body and wherein the arcuate internal bore is sized to permit advancement of an orthopedic implant therethrough;
   an arcuate plunger that slidably fits within the arcuate internal bore of the curved elongate body, the plunger having a proximal end and a conical distal end and wherein, when the plunger is positioned in the arcuate internal bore, the proximal end of the plunger protrudes out of the proximal opening of the arcuate internal bore and a conical distal end of the plunger protrudes out of the distal opening of the arcuate internal bore, and wherein the plunger prevents delivery of the implant by the insertion device through the arcuate internal bore when the plunger is positioned within the arcuate internal bore;
   an orthopedic implant sized to be advanced through the arcuate internal bore of the insertion device and into the skeletal system.

2. An instrument as in claim 1, further comprising one or more couplers that can be anchored between the pair of skeletal segments, wherein the distal end of the mount removably mounts to the coupler.

3. An instrument as in claim 1, wherein the insertion device pivots about a pivot axis such that a distal end of the curved elongate body pivots toward the space between the pair of skeletal segments.

4. An instrument as in claim 1, wherein the plunger has a sharpened tip.

5. An instrument as in claim 1, wherein the insertion device is removably attached to the proximal end of the mount.

6. An instrument for implanting an orthopedic implant into a target space between skeletal segments, comprising:
   an insertion device having a straight member and a curved elongate body extending from the straight member, wherein the curved elongate body has a proximal end attached to the straight member and wherein the curved elongate body contains an arcuate internal bore extending along a first axis from a proximal opening at a proximal region of the curved elongated body to a distal opening at a distal region of the curved elongated body and wherein at least a portion of the internal bore extends along the first axis from the proximal opening toward the distal opening in a curved trajectory, and wherein the internal bore, the proximal opening, and the distal opening are sized to permit advancement of the orthopedic implant therethrough;
   a mount that is positionable at a defined anatomical relationship relative to the target space between the skeletal segments, wherein the mount attaches to the straight member of the insertion device at a proximal end of the insertion device and, when attached to the insertion device, the mount limits movement of the insertion device relative to the skeletal segments; and
   an orthopedic implant that is adapted to implant into the target space, wherein the implant is sized to be advanced through the arcuate internal bore and into the target space.

7. An instrument as in claim 6, wherein the mount comprises a coupler that is adapted to anchor onto at least a portion of the skeletal segments.

8. An instrument set for use in a surgical procedure on a segment of a vertebral column that includes a first vertebral bone, a second vertebral bone, and an intervening disc space, comprising:
   an insertion device adapted to advance an orthopedic implant onto the segment, the insertion device comprising a proximal end, a distal end, and an elongated body positioned between the proximal end and the distal end, the elongate body containing an internal bore that extends along a first axis from an opening in the proximal end of the insertion device to an opening in the distal end of the insertion device, wherein at least a portion of the internal bore extends along the first axis in a curvilinear trajectory, and wherein the internal bore is sized to permit advancement of the implant through the arcuate internal bore and onto the segment;
   at least one anchor device having a first region that attaches with the proximal end of the insertion device at the proximal end of the insertion device and a second region attaches onto a surface with defined spatial relationship to the disc space, wherein the anchor, when attached to the insertion device, limits the movement of the insertion device relative to the disc space; and an orthopedic implant that is adapted to implant onto the segment, wherein the implant is sized to be advanced through the arcuate internal bore.

9. An instrument set as in claim 8, further comprising a plunger that slidably positions within the internal bore of the elongate body, and wherein, when the plunger is positioned in the internal bore, a proximal end of the plunger protrudes out of the proximal opening of the insertion device and a distal end of the plunger protrudes out of the distal opening of the insertion device.

10. An instrument set as in claim 9, wherein the plunger, when seated within the internal bore, prevents the delivery of the implant by the insertion device through the internal bore.

11. An instrument set as in claim 8, wherein the insertion device is aimed toward a target location using an x-ray image.

12. An instrument set for use in a surgical procedure on a segment of a vertebral column that includes a first vertebral bone, a second vertebral, and an intervening disc space, comprising:
   an insertion device adapted to advance an orthopedic implant onto the segment, the insertion device comprising a proximal end, a distal end, and a curved elongated body positioned between the proximal end and the distal end, the curved elongate body containing an arcuate internal bore that extends between an opening in the proximal end of the insertion device to an opening in the distal end of the insertion device, wherein the arcuate internal bore is sized to permit advancement of an implant through the arcuate internal bore and onto the segment;
   at least one anchor device having a first region that couples with the proximal end of the insertion device and a second region attaches onto a surface with a defined spatial relationship to the disc space, wherein the anchor, when attached to the insertion device, limits movement of the insertion device relative to the disc space; and
   a plunger that slidably positions within the arcuate internal bore of the curved elongate body, and wherein, when the plunger is positioned in the arcuate internal bore, a proximal end of the plunger protrudes out of the proximal opening of the insertion device and a distal end of the plunger protrudes out of the distal opening of the insertion device, and wherein the plunger, when positioned within the arcuate internal bore, prevents delivery of the implant by the insertion device through the arcuate internal bore.

13. An instrument set as in claim 12, further comprising orthopedic implant that is implantable at the segment, wherein the implant is sized to be advanced through the arcuate internal bore of the insertion device.

14. An instrument set as in claim 8, wherein the at least one anchor device is comprised of more than one segment.

15. An instrument set as in claim 8, wherein the at least one anchor device comprises a plurality of segments that are adapted to cooperatively attach to one another to collectively form the anchor device.

16. An instrument set as in claim 8, wherein the at least one anchor device comprises a first anchor segment and a second anchor segment and wherein the first anchor segment is adapted to articulate with the second anchor segment.

17. An instrument set as in claim 16, wherein the first anchor segment forms a ball and socket articulation with the second anchor segment.

18. An instrument set as in claim 8, wherein the at least one anchor device contains a deployable locking mechanism that is adapted to reversibly transition from a first position to a second position, and wherein the at least one anchor device includes a plurality of anchor segments are movable relative to one another when the locking mechanism is in the first position, and wherein the anchor segments are rigidly affixed to one another when the locking mechanism is transitioned into the second position.

19. An instrument set as in claim 8, wherein the at least one anchor device contains a deployable locking mechanism that is adapted to reversibly transition from a first position to a second position, wherein the at least one anchor device is movable relative to the target segment of the vertebral column when the locking mechanism is in the first position and wherein the anchor is immobilized relative to the segment of the vertebral column when the locking mechanism is transitioned into the second position.

20. An instrument set for use in a surgical procedure on a target segment of a skeletal member, comprising:
   an insertion device adapted to advance an orthopedic implant onto the target segment, the insertion device comprising a proximal segment, a distal segment, and an elongated body that extends in a first direction from the proximal segment to the distal segment, wherein the elongated body extends in a curvilinear trajectory along the first direction, wherein the elongated body contains an internal bore, and wherein the internal bore is sized to permit advancement of an orthopedic implant through the internal bore and onto the target segment of the skeletal member;
   at least one anchor device having a first region that is adapted to directly attach onto the proximal segment of the insertion device and a second segment that is adapted to attach onto a surface with defined spatial relationship to the target segment of the skeletal member, wherein the anchor device, when attached to the insertion device, limits the movement of the insertion device relative to the target segment of the skeletal member;
   the orthopedic implant adapted to implant onto the target segment of the skeletal member, wherein the orthopedic implant is sized to be advanced through the internal bore of the elongated body and wherein the orthopedic implant follows a curvilinear trajectory when advanced along the first direction of the elongated body from the proximal segment, through the internal bore and onto the spinal segment.

21. An instrument set for use in a surgical procedure on a target segment of a skeletal member, comprising:
   an insertion device adapted to advance an orthopedic implant onto the target segment, the insertion device comprising a proximal segment, a distal segment, and an elongated body that extends in a first direction from the proximal segment to the distal segment;
   wherein the elongated body contains a bore that is at least partially contained within the elongated body, wherein at least a portion of the internal bore extends along the first direction of the elongated body in a curvilinear trajectory, and wherein the internal bore is sized to permit advancement of an orthopedic implant through the internal bore and onto the spinal segment;
   a mount having a first segment and a second segment, wherein the first segment of the mount is postionable at a defined anatomical relationship relative to the target segment of the skeletal member, wherein the second segment of the mount attaches to the proximal segment of the insertion device, and, when attached to the insertion device, the mount limits movement of the insertion device relative to the skeletal member; and
   the orthopedic implant that is adapted to be implanted onto the target segment, wherein the orthopedic implant is sized to be advanced through the internal bore of the insertion device and onto the target segment.

22. An instrument set as in claim 21, wherein the elongated body extends outwardly in a first direction from the distal aspect of a straight member of the insertion device.

23. An instrument set as in claim 21, wherein the orthopedic implant follows a curvilinear trajectory when advanced along the first direction of the elongated body, through the internal bore and onto the target segment.

24. An instrument set as in claim 22, wherein a curvilinear segment of the internal bore of the elongated body has a radius that is substantially equal to the length of the straight member.

25. An instrument set as in claim 21, wherein the mount is comprised of a plurality of segments that are adapted to cooperatively attach to one another.

26. An instrument set as in claim 21, wherein the mount comprises a first segment and a second segment, and wherein the first segment of the mount is adapted to articulate with the second segment of the mount.

27. An instrument set as in claim 21, wherein the mount comprises a first segment and a second segment, wherein the first segment of the mount forms a ball and socket articulation with the second segment of the mount.

28. An instrument set as in claim 21, wherein the mount includes a deployable locking mechanism that is adapted to reversibly transition from a first position to a second position, wherein the mount includes a plurality of mount segments movable relative to one another when the locking mechanism is in the first position, and wherein the plurality of mount segments are rigidly affixed to one another when the locking mechanism is transitioned into the second position.

29. An instrument set as in claim 21, wherein the mount includes a deployable locking mechanism that is adapted to reversibly transition from a first position to a second position, wherein the mount is movable relative to the target segment when the locking mechanism is in the first position and wherein the mount is immobilized relative to the target segment when the locking mechanism is transitioned into the second position.

30. An instrument set as in claim 6, wherein the at least one mount is comprised of more than one segment.

31. An instrument set as in claim 6, wherein the at least one mount comprises a plurality of segments that are adapted to cooperatively attach to one another to collectively form the mount.

32. An instrument set as in claim 6, wherein the at least one mount comprises a first mount segment and a second mount segment and wherein the first mount segment is adapted to articulate with the second mount segment.

33. An instrument set as in claim 32, wherein the first mount segment forms a ball and socket articulation with the second mount segment.

34. An instrument set as in claim 6, wherein the at lease one mount contains a deployable locking mechanism that is adapted to reversibly transition from a first position to a second position, and wherein the at least one mount includes a plurality of segments that are movable relative to one another when the locking mechanism is in the first position, and wherein the segments are rigidly affixed to one another when the locking mechanism is transitioned into the second position.

35. An instrument set as in claim 6, wherein the at lease one mount contains a deployable locking mechanism that is adapted to reversibly transition from a first position to a second position, wherein the at least one mount is movable relative to the target segment of the vertebral column when the locking mechanism is in the first position and wherein the mount is immobilized relative to the segment of the vertebral column when the locking mechanism is transitioned into the second position.

* * * * *